(12) United States Patent
Ahmed (10) Patent No.: US 10,603,220 B2
(45) Date of Patent: Mar. 31, 2020

(54) CRANIAL CAP DRESSING

(71) Applicant: Osama Ahmed, Shreveport, LA (US)

(72) Inventor: Osama Ahmed, Shreveport, LA (US)

(73) Assignee: BOARD OF SUPERVISORS OF LOUISIANA STATE UNIVERSITY, Baton Rouge, LA (US)

( * ) Notice: Subject to any disclaimer, the term of this patent is extended or adjusted under 35 U.S.C. 154(b) by 646 days.

(21) Appl. No.: 15/192,002

(22) Filed: Jun. 24, 2016

(65) Prior Publication Data

US 2016/0374864 A1 Dec. 29, 2016

Related U.S. Application Data

(60) Provisional application No. 62/185,933, filed on Jun. 29, 2015.

(51) Int. Cl.
*A61F 13/00* (2006.01)
*A61F 13/12* (2006.01)

(52) U.S. Cl.
CPC ........ *A61F 13/12* (2013.01); *A61F 13/00029* (2013.01); *A61F 13/00042* (2013.01); *A61F 13/00046* (2013.01); *A61F 2013/00217* (2013.01); *A61F 2013/00251* (2013.01)

(58) Field of Classification Search
CPC ....................................................... A61F 13/12
USPC ................................................... 602/41, 46
See application file for complete search history.

(56) References Cited

U.S. PATENT DOCUMENTS

| | | | | |
|---|---|---|---|---|
| 2,726,398 A | * | 12/1955 | Cooper | A42B 1/12 2/68 |
| 3,370,304 A | * | 2/1968 | Pelletier | A42B 1/061 2/174 |
| 3,512,181 A | * | 5/1970 | Osborne | A42B 1/043 2/181.2 |
| 4,279,039 A | * | 7/1981 | Drew | A42B 1/12 2/428 |
| D295,446 S | * | 4/1988 | Lundell | D2/867 |
| 4,937,885 A | * | 7/1990 | Gregg | A42B 1/006 2/171 |
| 5,031,609 A | * | 7/1991 | Fye | A61F 13/12 128/857 |
| 5,571,079 A | * | 11/1996 | Bello | A61F 13/0203 602/46 |
| 6,664,434 B2 | * | 12/2003 | Cominsky | A61F 15/004 128/888 |
| 7,887,501 B2 | * | 2/2011 | Riordan | A61F 13/12 424/445 |
| 8,262,601 B2 | * | 9/2012 | Cumming | A61F 13/12 2/171 |
| 9,149,393 B2 | * | 10/2015 | Cumming | A61F 13/12 |
| 2005/0262617 A1 | * | 12/2005 | Szypka | A61F 13/12 2/410 |
| 2009/0216169 A1 | * | 8/2009 | Hansen | A61F 15/001 602/48 |

FOREIGN PATENT DOCUMENTS

GB 763721 A * 12/1956 ............. A42B 1/043

* cited by examiner

*Primary Examiner* — Kim M Lewis
(74) *Attorney, Agent, or Firm* — Davis & Bujold PLLC; Charles Holoubek (57) ABSTRACT

A cranial cap dressing for dressing a craniotomy wound comprising a breathable elastic outer layer sized to fit snuggly on a human head of a patient and an absorbent inner layer attached to the breathable elastic outer layer.

1 Claim, 6 Drawing Sheets

CRANIAL CAP DRESSING

CROSS REFERENCE TO RELATED APPLICATIONS/PRIORITY

The present invention claims priority to U.S. Provisional Patent Application No. 62/185,933 filed Jun. 29, 2015, which is incorporated by reference into the present disclosure as if fully restated herein. To the extent that there is any conflict between the incorporated material and the present disclosure, the present disclosure will control.

FIELD OF THE INVENTION

The present invention relates generally to surgical dressing and specifically to a cranial cap dressing.

BACKGROUND OF THE INVENTION

Long-term placement of a sterile dressing after a craniotomy can be difficult to manage. Completely shaving the patient's hair can be traumatic to the patient. Therefore, to maintain comesis, minimal hair shaving is practiced by neurosurgeons. As a consequence of minimal hair shaving though, adhesive dressings cannot stay secured to the incision site without the use of mechanical attachment such as staples. However, the use of staples is not preferred by many surgeons and patients. An alternative to adhesive dressing is the use linear wrap bandages, such as ACE® wrap elastic bandage and/or Kerlix® gauze wrap bandages to wrap the head. One problem with the linear wrap bandages is that they can be easily removed by the patient if the patient has an altered mental status and/or is unable to follow and/or remember simple instructions. Many times patients having altered mental status will pick at the wound site dressing if not covered. A second problem with the linear wrap bandages is that when a patient lies down on his bed and moves his head with relation to the pillow, the linear wrap bandage will many times roll up, exposing previously covered skin. These problems can expose patients to wound infections, thus leading to longer hospital stays, more surgical interventions, and higher costs of medical care.

SUMMARY OF THE INVENTION

Wherefore, it is an object of the present invention to overcome the above mentioned shortcomings and drawbacks associated with the prior art.

Another object of the present invention is to provide a sterile cranial cap dressing with draw strings to provide a sterile barrier over the surgical site.

A further object of the present invention is to reduce the infection rate post craniotomy.

Yet another object of the present invention is to secure placement of craniotomy surgical dressing.

A still further object of the present invention is to increase the speed and accuracy in which craniotomy surgical dressing is applied.

The present invention also relates to a cranial cap dressing for dressing a craniotomy wound comprising a breathable elastic outer layer sized to fit snuggly on a human head of a patient and an absorbent inner layer attached to the breathable elastic outer layer.

The present invention relates to methods of dressing a craniotomy and cranial cap dressings for dressing a human craniotomy wound comprising a breathable elastic outer layer sized to fit snuggly on a head of a human patient, and an absorbent inner layer attached to the breathable elastic outer layer.

An optional further embodiment includes a plurality of breathing channels in the absorbent inner layer providing a passageway for air through the absorbent inner layer to the breathable elastic outer layer.

An optional further embodiment includes a contact film polymer layer coating on a proximal skin facing surface of the inner layer that reduces the adhesion of the inner layer to the wound. An optional further embodiment includes a plurality of perforations in the contact film polymer layer coating to allow air and bodily fluids to pass through the contact film polymer layer coating.

An optional further embodiment includes a mechanical fastener along a circumference of the cranial cap dressing, which helps secure the cranial cap dressing on the head of the patient. An optional further embodiment includes the mechanical fastener being one of a Velcro® flap, a button, a snap, a latch, a buckle, a fabric tie, and a string tie. An optional further embodiment includes the mechanical fastener being located at an inferior posterior most portion of the cranial cap dressing. An optional further embodiment includes the mechanical fastener being a string tie and further comprising a string substantially further comprising a substantially non-elastic string extending in a channel around the circumference of the cranial cap dressing.

An optional further embodiment includes an anti-microbial agent being affixed to a proximal surface of the inner layer. An optional further embodiment includes the antimicrobial agent being one of elemental or ionic silver. An optional further embodiment includes the antimicrobial agent being one of silver nitrate and silver sulfadiazine.

An optional further embodiment includes the breathable elastic outer layer having a coefficient of static friction between two pieces of the same material being less than 0.3.

An optional further embodiment includes a proximate breathable layer attached to the inner layer, opposite to the outer layer.

An optional further embodiment includes a maximum thickness of the inner layer being greater in an area corresponding to an incision than a maximum thickness of the inner layer in an area spaced from the area corresponding to the incision.

An optional further embodiment includes the inner layer being formed as a checkered pattern of absorbent material lining a proximal skin facing surface of the outer layer.

An optional further embodiment includes the inner layer being a substantially a continuous layer of absorbent material extending substantially completely across a proximal skin facing surface of the outer layer. An optional further embodiment includes a plurality of perforations through the inner layer to provide breathing channels for vapor to pass through the inner layer to the outer layer.

An optional further embodiment includes a medical adhesive or gel affixed to a circumference of the cranial cap dressing to help releasably secure the cranial cap dressing to a skin of the patient.

An optional further embodiment includes the cranial cap dressing substantially completely covering a cranium of the patient.

An optional further embodiment includes one or more flap that may be folded down to cover incisions that extend below a circumference of the cranial cap dressing.

BRIEF DESCRIPTION OF THE DRAWINGS

The accompanying drawings, which are incorporated in and constitute a part of the specification, illustrate various embodiments of the invention and together with the general description of the invention given above and the detailed description of the drawings given below, serve to explain the principles of the invention. It is to be appreciated that the accompanying drawings are not necessarily to scale since the emphasis is instead placed on illustrating the principles of the invention. The invention will now be described, by way of example, with reference to the accompanying drawings in which.

DETAILED DESCRIPTION OF THE INVENTION

The present invention will be understood by reference to the following detailed description, which should be read in conjunction with the appended drawings. It is to be appreciated that the following detailed description of various embodiments is by way of example only and is not meant to limit, in any way, the scope of the present invention. In the summary above, in the following detailed description, in the claims below, and in the accompanying drawings, reference is made to particular features (including method steps) of the present invention. It is to be understood that the disclosure of the invention in this specification includes all possible combinations of such particular features, not just those explicitly described. For example, where a particular feature is disclosed in the context of a particular aspect or embodiment of the invention or a particular claim, that feature can also be used, to the extent possible, in combination with and/or in the context of other particular aspects and embodiments of the invention, and in the invention generally. The term "comprises" and grammatical equivalents thereof are used herein to mean that other components, ingredients, steps, etc. are optionally present. For example, an article "comprising" (or "which comprises") components A, B, and C can consist of (i.e., contain only) components A, B, and C, or can contain not only components A, B, and C but also one or more other components. Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

The term at "least" followed by a number is used herein to denote the start of a range beginning with that number (which may be a range having an upper limit or no upper limit, depending on the variable being defined). For example "at least 1" means 1 or more than 1. The term "at most" followed by a number is used herein to denote the end of a range ending with that number (which may be a range having 1 or 0 as its lower limit, or a range having no lower limit, depending upon the variable being defined). For example, "at most 4" means 4 or less than 4, and "at most 40%" means 40% or less than 40%. When, in this specification, a range is given as "(a first number) to (a second number)" or "(a first number)-(a second number)," this means a range whose lower limit is the first number and whose upper limit is the second number. For example, 25 to 100 mm means a range whose lower limit is 25 mm, and whose upper limit is 100 mm. The embodiments set forth the below represent the necessary information to enable those skilled in the art to practice the invention and illustrate the best mode of practicing the invention. In addition, the invention does not require that all the advantageous features and all the advantages need to be incorporated into every embodiment of the invention.

Turning now to FIGS. 1-5, a brief description concerning the various components of the present invention will now be briefly discussed. As can be seen in this embodiment, the cranial cap dressing 2 comprises and an outer layer 4 and an inner layer 6. The outer layer 6 is preferably stretchable and breathable and allows application of the cranial cap dressing 2 to at least a variety of head 8 sizes for different patients. The outer layer 4 can be comprised of normal and/or microfiber designs of synthetic and/or natural fiber alone or in a blend with each other and/or an additional elastic fiber elastic element 34. The synthetic fibers include polyester, nylon, rayon, acetate, ingeo, lyocell, olefin, and polylactide, for example. The natural fibers include cotton and flax, for example. The elastic fibers can include spandex, for example. The outer layer 4 material should be porous enough to provide breathability or ready vapor passage 10 to avoid excessive sweating while wearing the cranial cap dressing 2. Excessive sweat can lead to periwound maceration among other issues.

The outer layer 4, while preferably elastic, is not meant to apply physiologically significant compressive force on the patient's head 8, which would be counterproductive for wound 12 healing. The elasticity is meant to be sufficient to fit a variety of head 8 sizes and to snuggly fit onto a patient's head 8 and remain in place without any additional binding. It is anticipated that four sizes of cranial cap dressings 2 will be sufficient for most of the population, from smallest to largest: being pediatric, teen, small adult, large adult. The outer layer 4 is designed to preferably not restrict or cut off blood circulation to the patient's head 8. The outer layer 4 is physical barrier protecting the wound 12 from the patient purposely or inadvertently picking at or disturbing the wound site 12. The outer layer 4 also provides scaffolding for the inner layer 6 bandage 14, holding the inner layer 6 in place on the surface 16 of the patient's head 8. The outer layer 4 can be of uniform elasticity and thickness, or it could have increased elasticity and/or thickness especially adjacent to the perimeter edges of the cranial cap dressing 2, to increase the chances that the cranial cap dressing 2 will stay in place as the patient moves in bed.

The inner layer 6 would be preferably comprised of an adsorbent material that allows for fluid absorption, such as blood, sweat and other body fluids, keeping the skin 16 and surgical site 12 appropriately dry. The inner layer 4 material may be cotton or cotton based, or other natural or synthetic adsorbent material. The inner layer is preferably 0.5 to 25 mm in thickness, more preferably 1 to 10 mm in thickness, most preferably 2 to 7 mm in thickness. The inner layer 6 may be in different designs, but should provide sufficient breathability that the patient does not excessively sweat while wearing the cranial cap dressing 2.

The skin 16 facing proximal surface 18 of the inner layer 6 preferably has a polyester wound contact film polymer 20, similar to Telfa™ "Ouchless" Non-Adherent Dressings, that contacts the patient's skin 16 but helps prevent the inner layer 6 from sticking to the patient's skin 16. The layer of contact film polymer 20 would allow the inner layer 6 to provide abortion of body fluids without substantially sticking to the patient's skin 16 or hair. The contact film polymer 20 would preferably have sufficient perforations 22, such as 382 holes per square inch, with each hole having a diameter of 0.020-0.030 inch, to allow moist vapor transmission and fluid transmission into the inner absorbent core 24 of the bandage 14 of the inner layer 6—between the contact film polymer 20 and the outer layer 2. The skin 16 facing proximal surface of the contact film polymer 20 is preferably impregnated with elemental or preferably ionic silver 26 to help promote wound healing without infection, in the form of silver nitrate or silver sulfadiazine, for example. If no contact film polymer 20 is used, the proximal surface 18 of the inner layer would preferably be impregnated with elemental or preferably ionic silver 26 to help promote wound healing without infection. Another anti-microbial agent 26 may be used in addition to or in place of the silver 26. Additionally, the silver 26 may be dispersed in the absorbent core 24 of the bandage 14 of the inner layer 6 to reduce bacterial growth in the absorbent core 24

Figure 3:
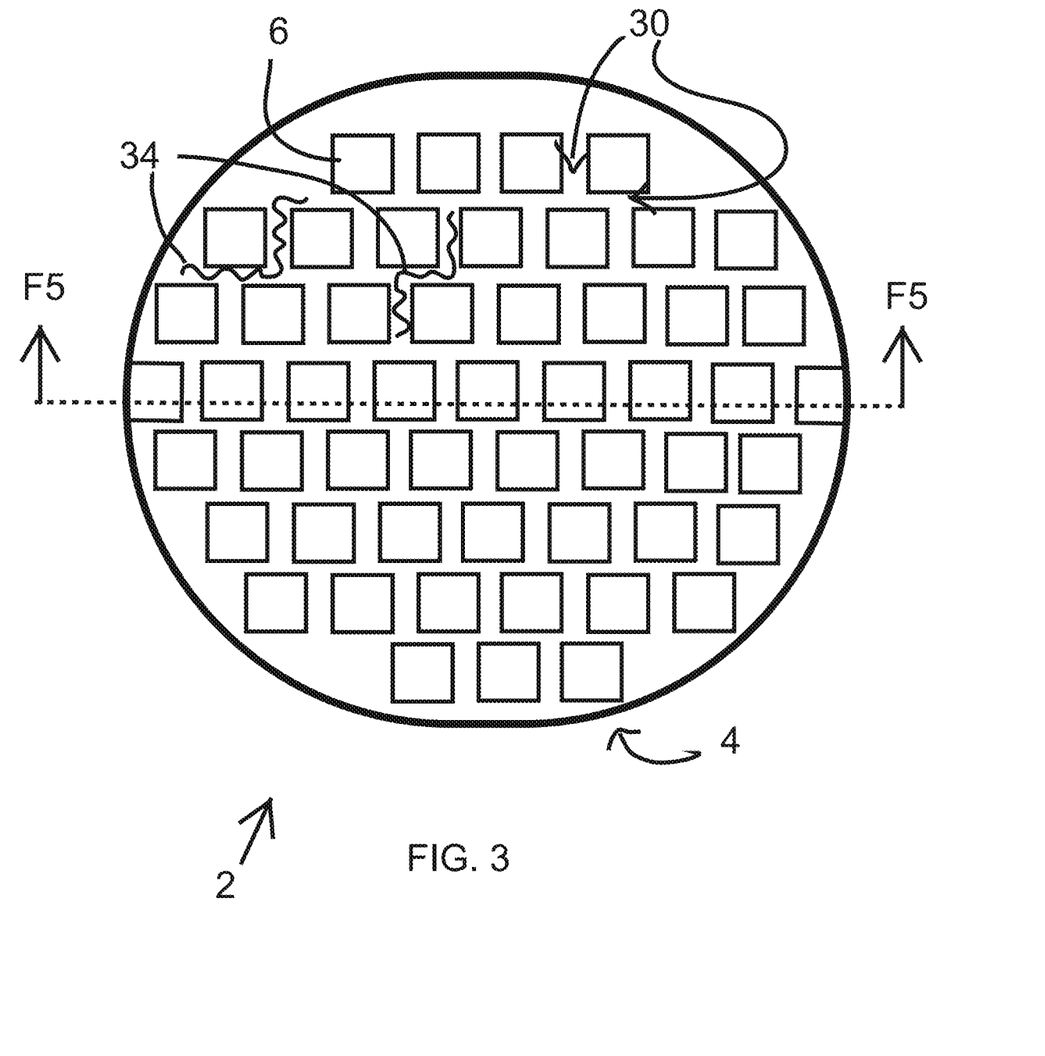
FIG. 3 is a diagrammatic representation of the inner lining of a first embodiment of the cranial cap dressing of FIG. 2 in the area indicated F3/F4.

In a first embodiment, as shown in FIG. 3, the inner layer 6 is formed as a checkered pattern of gauze 14 lining the proximal surface 28 of the outer layer 4, with gaps or preferably unobstructed breathing channels 30 between adjacent gauze pads 14. The breathing channels 30 facilitate the vapor passage 10 or passage of humid air and heat from the skin 16 of the patient between the inner layer gauze pads 14, through the outer layer 4. The distal surface 32 (facing away from the patient) of the inner layer 6, here the gauze pads 14, would be affixed, preferably mechanically or chemically, to the proximal surface 28 of the outer layer 28.

Figure 4:
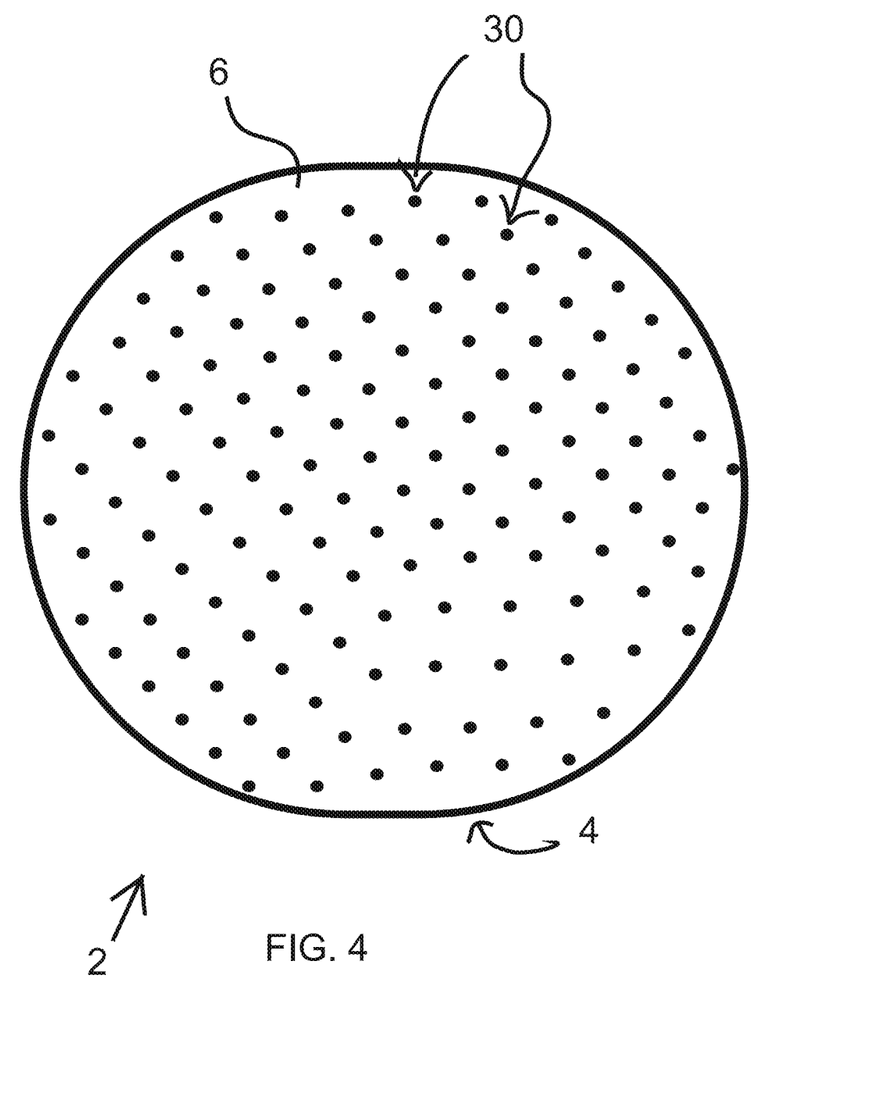
FIG. 4 is a diagrammatic representation of the inner lining of a second embodiment of the cranial cap dressing analogous with the area indicated F3/F4 in FIG. 2.

Alternatively or additionally, as shown in FIG. 4, the inner layer 6 could be a continuous layer of absorbent fabric or material 14 with perforations through the material to provide breathing channels 30. Though breathing channels 30 are preferred, if the inner layer 6 material is itself sufficiently breathable, the distinct breathing channels 30 may be omitted.

The inner layer 6 could be non-elastic, or could have an elastic element 34 integrated or woven within the inner layer 6. The elastic element could be integrated throughout the inner layer 6, or in just specific locations, like in the breathing channels 30, for example. The elastic elements 34 could include a plurality of single spandex micro-fiber strands.

Figure 5:
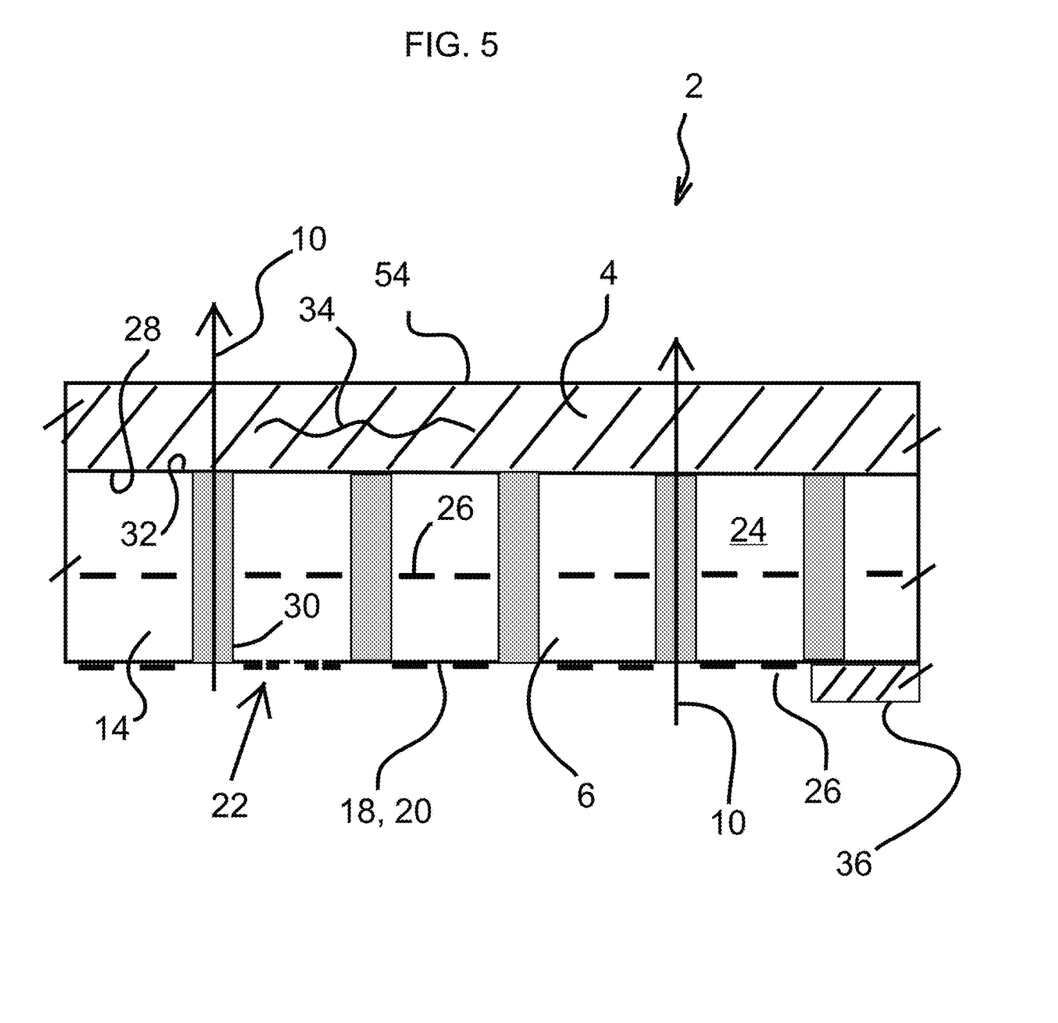
FIG. 5 is a diagrammatic representation of a cross section of FIG. 3 along the view indicated as F5.

Additionally, a proximal stretchable breathable layer 36, similar to the outer layer 4 material, could line the proximal surface 18 of the inner layer 6, shown partially in FIG. 5. In this embodiment the cranial cap dressing 2 would have an absorbent inner layer 6 sandwiched between two stretchable breathable layers 4, 36. The proximal breathable layer 36 may have a perforated contact film polymer lining 20 on the proximal surface which contacts the patient's skin, to help prevent sticking to the wound, skin, or hair, which may also be impregnated or lined with anti-microbial agent 26.

Figure 1:
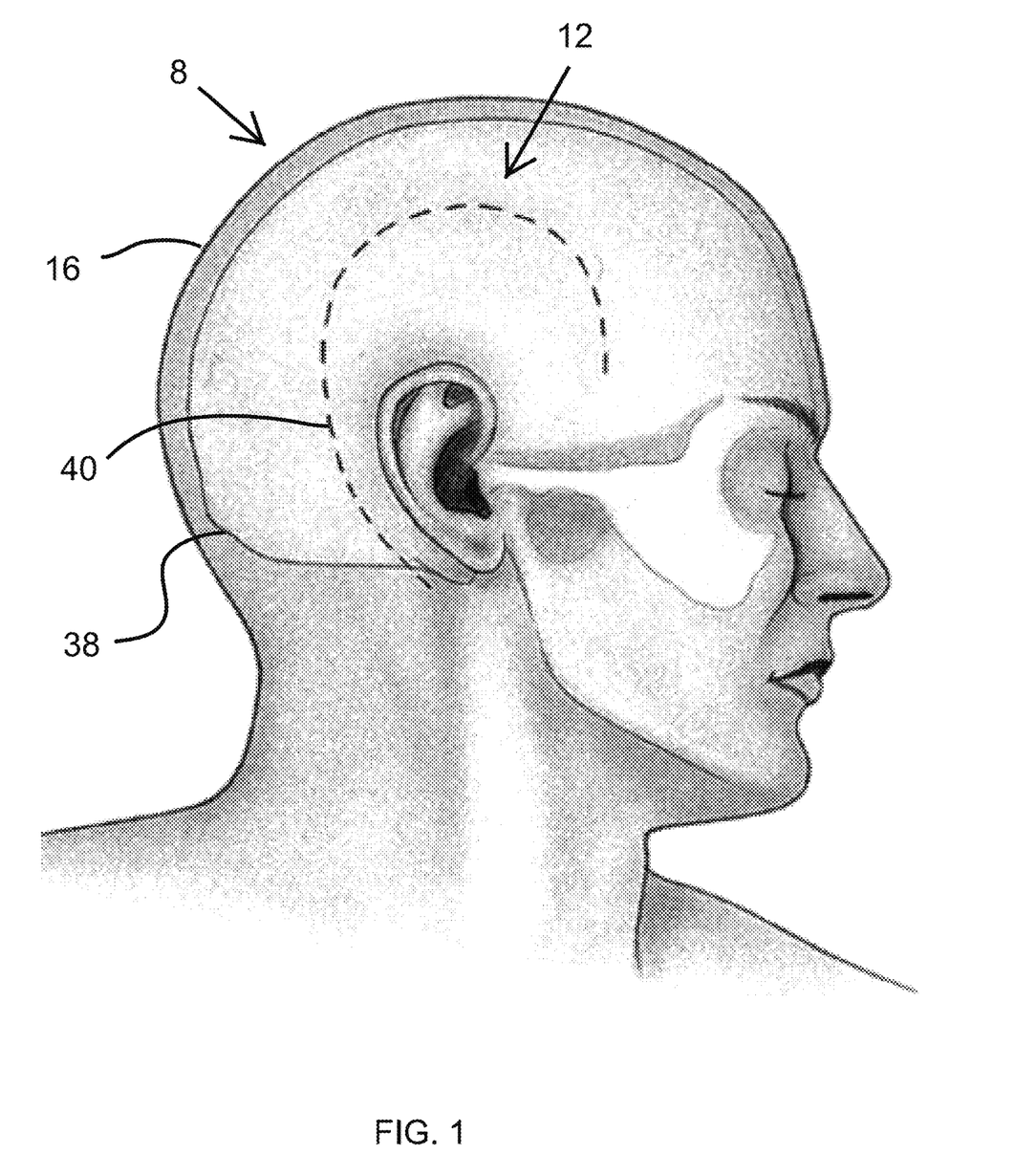
FIG. 1 is a drawing of a human patient with the cranium location indicated.
Figure 2:
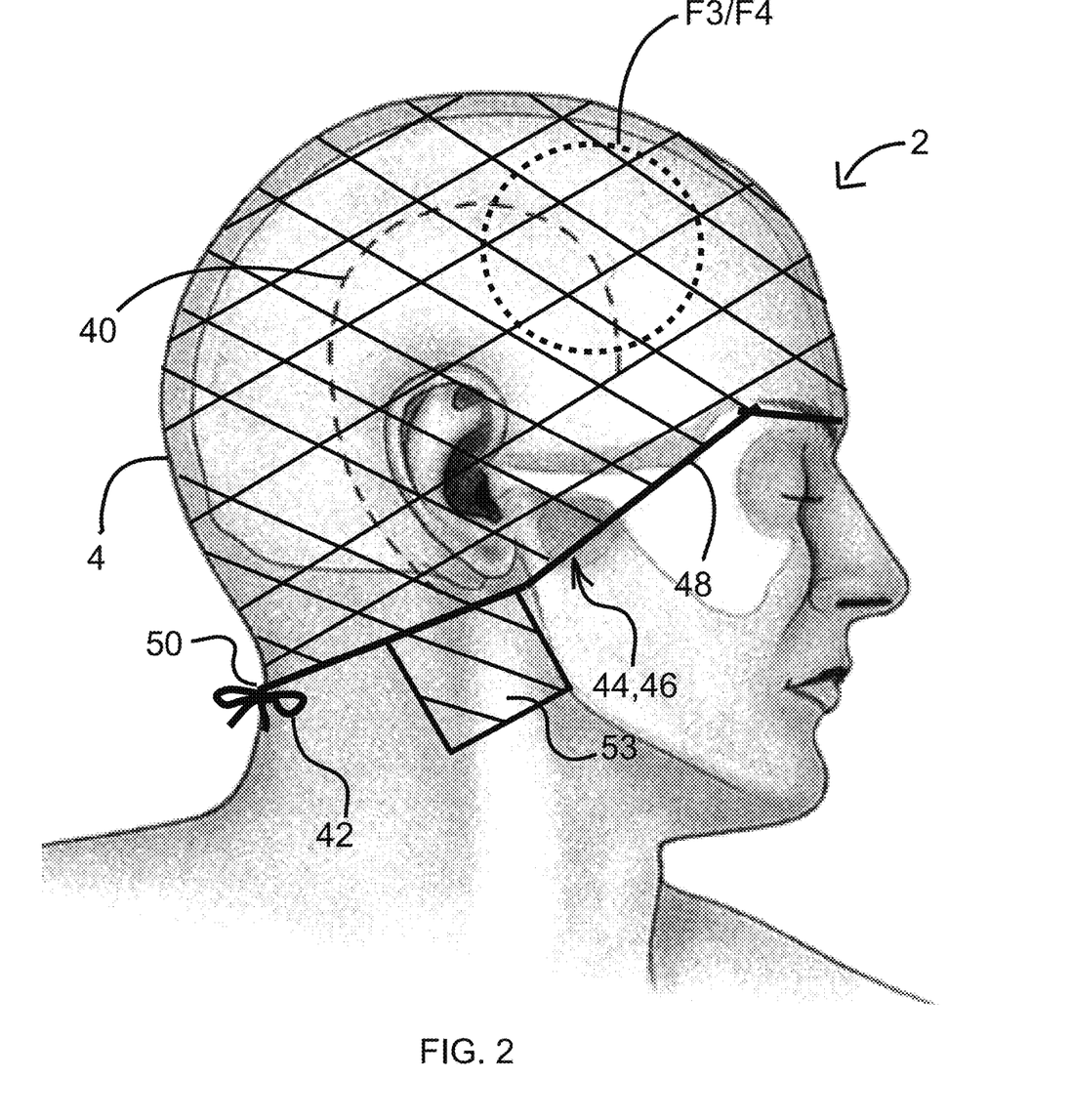
FIG. 2 is a diagrammatic representation of the cranial cap dressing according to the present invention, with the cranial cap dressing represented as hatched lines to allow context of the cranial cap dressing's placement.

Turning again to FIG. 1, the cap would provide circumferential coverage over a cranium 38 to allow coverage of a craniotomy incision 40 at basically any location. Shown in FIGS. 1 and 2 is a typical incision site for a temporal craniotomy, but the cap is designed to be used for dressing incisions of various craniotomies. These various craniotomies include, for example, the pterional and frontotemporal craniotomy incisions, which normally extend from the zygomatic arch 1 cm in front of the tragus, curves anteriorly, remains behind the hairline, and ends at widow's peak; the frontal craniotomy (unilateral or bilateral) incisions, in which unilateral approach uses an incision starting less than 1 cm anterior to the tragus and just above the zygomatic arch, curves superiorly and posteriorly, and ends at the midline frontally and the bilateral approach uses an ear-to-ear incision (also known as a bicoronal incision) that is also less than 1 cm anterior to the tragus and terminates on each side just above the zygomatic arches while remaining behind the hairline; the temporal craniotomy incisions (shown), which may be linear or question-mark depending on the target pathology, where linear incisions normally stay within the temporalis muscle and begin anterior to the tragus, 1-2 cm above the zygomatic arch, and extend anywhere from 6-8 cm above the arch; question-mark incisions also run anterior to the tragus, begin just above the zygomatic arch, and curve posteriorly at the top of the pinna 6-9 cm, then superiorly to the superior temporal line, then anteriorly toward the forehead, terminating at the hairline; and the suboccipital craniotomy/craniectomy incisions, which involve a few incision types, including midline and paramedian incisions that are linear, midline incision extends from 6 cm above the inion to the C2 spinous process; paramedian incision (also referred to as a retrosigmoid approach) begins 5 mm medial to the mastoid notch and extends 4-6 cm above and below the notch, "hockey-stick" incisions are curved and begin in the midline at the C2 spinous process, extend superiorly to just above the inion, and then laterally to mastoid tip with a terminal caudal curve.

Figure 6:
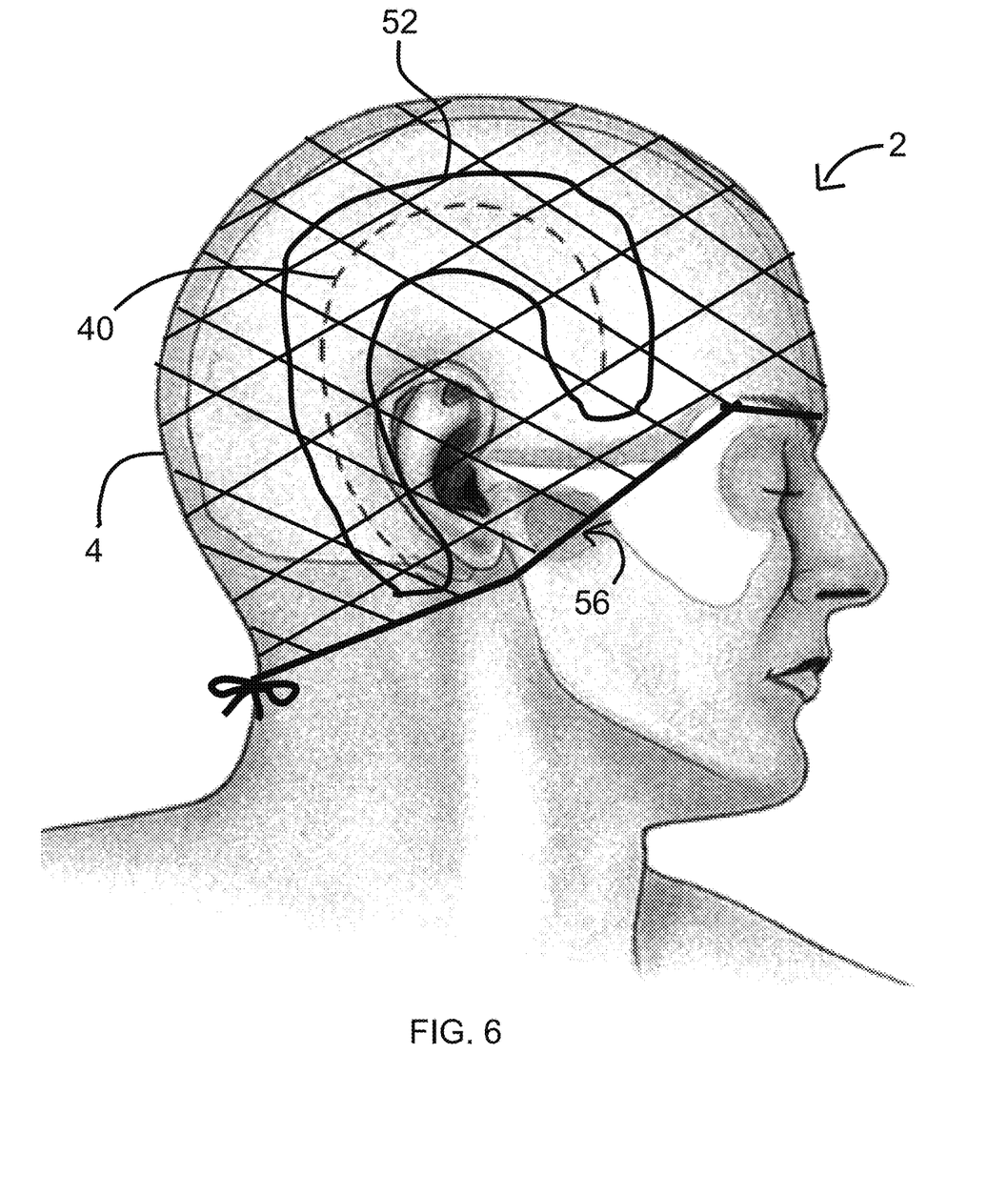
FIG. 6 is a diagrammatic representation of a further embodiment of the cranial cap dressing according to the present invention, with the cranial cap dressing represented as hatched lines to allow context of the cranial cap dressing's placement.

In further embodiments, the inner layer 6 may have a greater average and/or maximum thickness 52 in an area of the cranial cap dressing 2 that overlaps or corresponds to an area of a typical incision for common craniotomies, including those listed above, than an average and/or maximum thickness in areas not overlapping not corresponding with the specific craniotomy. For example, the cranial cap dressing 2 shown in FIG. 6 is for a question mark temporal craniotomy. Separate cranial cap dressings 2 could be available for the different common craniotomies in the different cranial cap dressing 2 sizes. The amount of overlap could vary, but would preferably be extend between 0.5 to 4 inches from either side of a typical incision 40, more preferably from 1 to 3 inches from either side of a typical incision 40, and most preferably from 1.5 to 2 inches from either side of a typical incision 40. The greater thickness 52 of the inner layer would preferably be from a relatively greater thickness 52 of bandage portion 14 of inner layer 6 around the area of the typical incision 40 than other areas of the cranial cap dressing 2. The relatively greater thickness 52 can be from extra thickness of the bandage portion 14 in the area of the typical incision 40, or from a normal thickness of the bandage portion 14 in the area of the typical incision 40 and a reduced or no thickness of the bandage portion 14 of the other areas of the cranial cap dressing 2. The relatively greater thickness 52 can allow for bandages 14 to adsorb any fluid from the incision/wound 12, 34. The relatively greater thickness will facilitate a relatively greater pressure being applied by the cranial cap dressing 2 at the wound location and simultaneously allow for increased heat and vapor transmission, increased comfort, and reduced pressure being applied in other areas cranial cap dressing 2 not associated with the incision 40.

In a variation of this embodiment, the bandage portion 14 of the cranial cap dressing 2 may initially extend substantially continuously in the cranial cap dressing 2, but may be perforated or otherwise pre-cut and preferably marked in multiple designs. The pre-cut/marked portions will preferably correspond to the areas of the typical incisions 40 for common craniotomies. In this way, a single cranial cap dressing 2 may be provided for multiple craniotomies, and then the surgeon could simply and easily remove the excess bandages from the bandage portion 14, and leave the bandage portion 14 that corresponds to the specific craniotomy incision 40 that the surgeon is performing on the patient.

As shown in FIG. 2, the cranial cap dressing 2 extends below the ears and down below the inion to the base of the neck. A string tie or other mechanical fastener 42 is preferably present as an extra security measure to help insure the cranial cap dressing 2 stays in place. A string 44, for example being continuous with the string tie 42, may extend in a channel 46 around the circumference 48 of the cranial cap dressing 2, with free ends extending out of opening 50 in the channel 46 at the posterior inferior terminus of the cranial cap dressing 2. The knotted string tie 42 portion could be left open, could be covered by a flap or it could fit in to a pocket on the interior or exterior of the cranial cap dressing 2. The string 44 could also just extend a portion of the way from the opening 50 into the channels 46, and not the full circumference 48 of the cranial cap dressing 2. Additionally, the string 44 and the mechanical fastener 42 at the posterior inferior terminus of the cranial cap dressing 2 may be discontinuous with one another. The string 44 is preferably substantially non-elastic. The placement of the string tie 42 is to minimize obstruction and maximize chances that a patient having an altered mental state will not bother it. Other extra security measure attachments could be used in addition or in place of the string 44 and/or string tie 42, including a Velcro® flap (being a closure consisting of a piece of fabric of small hooks that sticks to a corresponding fabric of small loops), buttons, snaps, latches, buckles, or fabric ties, for example. There could be more than one extra security measure attachment, though one is preferred for ease of use. The string tie 42 or other extra security measure attachment could be placed at other locations, but the posterior inferior terminus of the cranial cap dressing 2 is preferred. Additionally, or alternatively to the string 44, another circumferential reinforcement could be provided along a portion of the circumference 48 of the cranial cap dressing 2. The portion being preferably a majority of the circumference 48 of the cranial cap dressing 2, and most preferably substantially the entire circumference 48 of the cranial cap dressing 2.

The cranial cap dressing 2 may have one or more flaps 53 that could be folded down to cover incisions 40 that extend below the circumference 48 or inferior edge of the cranial cap dressing 2. The cranial cap dressing 2 may also be rolled up from the back for comfort if the incision site 40 was in another location.

While in the preferred embodiment, substantially the entire outer layer 4 has a uniform elasticity, in further embodiments different areas of the outer layer 4 may be of different elasticities, with, for example, an area around the incision 40 having a greater elasticity than other areas of the cranial cap dressing 2. In yet further embodiments, a distal surface 54 (facing away from patient) of the outer layer 4 has a low coefficient of static friction to minimize the interaction between the cranial cap dressing 2 and a patient's sheets, pillowcases, and bed coverings, thus reducing relative movement of the cranial cap dressing 2 and the patient's skin 16—preferably with a coefficient of static friction between two pieces of the same material being less than 0.3, more preferably being less than 0.2, and most preferably being less than 0.1. In yet further embodiments, a removable medical adhesive or gel 56 is attached to the circumference 48 of the cranial cap dressing 2, to help the cranial cap dressing 2 maintain its coverage over the head 8 of the patient.

The invention illustratively disclosed herein suitably may explicitly be practiced in the absence of any element which is not specifically disclosed herein. While various embodiments of the present invention have been described in detail, it is apparent that various modifications and alterations of those embodiments will occur to and be readily apparent those skilled in the art. However, it is to be expressly understood that such modifications and alterations are within the scope and spirit of the present invention, as set forth in the appended claims. Further, the invention(s) described herein is capable of other embodiments and of being practiced or of being carried out in various other related ways. In addition, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items while only the terms "consisting of" and "consisting only of" are to be construed in the limitative sense.

Wherefore, I claim:

1. A cranial cap dressing for dressing a human craniotomy wound comprising:
    a breathable elastic outer layer sized to fit snuggly on a head of a human patient;
    an absorbent inner layer attached to the breathable elastic outer layer;
    a plurality of breathing channels in the absorbent inner layer providing a passageway for air through the absorbent inner layer to the breathable elastic outer layer;
    a contact film polymer layer coating on a proximal skin facing surface of the inner layer that reduces the adhesion of the inner layer to the wound;
    a plurality of perforations in the contact film polymer layer coating to allow air and bodily fluids to pass through the contact film polymer layer coating;
    a mechanical fastener along a circumference of the cranial cap dressing, which helps secure the cranial cap dressing on the head of the patient;
    the mechanical fastener is one of a Velcro flap, a button, a snap, a latch, a buckle, a fabric tie, and a string tie;
    the mechanical fastener is located at an inferior posterior most portion of the cranial cap dressing;
    the mechanical fastener is a string tie and further comprising a string substantially further comprising a substantially non-elastic string extending in a channel around the circumference of the cranial cap dressing;
    an anti-microbial agent is affixed to a proximal surface of the inner layer;
    the antimicrobial agent is one of elemental or ionic silver;
    the antimicrobial agent is one of silver nitrate and silver sulfadiazine;
    the breathable elastic outer layer having a coefficient of static friction between two pieces of the same material being less than 0.3;

a proximate breathable layer attached to the inner layer, opposite to the outer layer;

a maximum thickness of the inner layer is greater in an area corresponding to an incision than a maximum thickness of the inner layer in an area spaced from the area corresponding to the incision;

the inner layer is formed as a checkered pattern of absorbent material lining a proximal skin facing surface of the outer layer;

the inner layer is a substantially a continuous layer of absorbent material extending substantially completely across a proximal skin facing surface of the outer layer;

a plurality of perforations through the inner layer to provide breathing channels for vapor to pass through the inner layer to the outer layer;

a medical adhesive or gel affixed to a circumference of the cranial cap dressing to help releasably secure the cranial cap dressing to a skin of the patient;

the cranial cap dressing substantially completely covers a cranium of the patient; and one or more flap that may be folded down to cover incisions that extend below a circumference of the cranial cap dressing.

\* \* \* \* \*